United States Patent [19]

Barr

[11] Patent Number: Plant 7,304

[45] Date of Patent: Aug. 21, 1990

[54] PITTOSPORUM TOBIRA 'HINES HARDY'

[75] Inventor: William C. Barr, Rosenberg, Tex.

[73] Assignee: Weyerhaeuser Company

[21] Appl. No.: 286,570

[22] Filed: Dec. 19, 1988

[51] Int. Cl.[5] ..... A01H 5/00

[52] U.S. Cl. ..... Plt./54

[58] Field of Search ..... Plt./54

*Primary Examiner*—Robert E. Bagwill

[57] ABSTRACT

A new cultivar of *Pittosporum tobira,* commonly known as Mock Orange or Japanese Pittosporum, characterized by a compact form and appearance and lustrous dark green foliage. The outstanding feature of the new cultivar is a winter hardiness at least adequate for USDA Zone 8 (10°-20° F.) and possibly for USDA Zone 7 (0°-10° F.)

1 Drawing Sheet

The present invention relates to a new and distinct plant cultivar of *Pittosporum tobira,* commonly known as Mock Orange or Japanese Pittosporum in the Pittosporaceae family.

DISCOVERY

This cultivar was discovered during the winter of 1981-1982 at Hines Nurseries, P.O. Box 42284, Houston, Tex. in a bed of *Pittosporum tobira* that were grown from seed. A single plant was selected out and isolated for further evaluation because it showed no sign of winter damage while other *Pittosporum tobira* in the same bed were damaged or destroyed.

REPRODUCTION

The new cultivar has been reproduced numerous times by asexual propagation (vegetative cuttings) at Hines Nurseries. The progeny exhibit similar appearance and growth habit to the parent and share its outstanding cold hardiness. This establishes the plant as reproducible and true to type.

OUTSTANDING CHARACTERISTIC

*Pittosporum tobira* 'Hines Hardy' has exhibited a unique and desirable attribute of superior winter hardiness. The plant has a very compact appearance and lustrous dark green foliage.

DESCRIPTION OF THE PHOTOGRAPH

The FIGURE, a photograph, exhibits the overall appearance of an individual plant of the new cultivar, growing in a five gallon container at the age of 18 months from cuttings.

DETAILED PLANT DESCRIPTION

The following is a detailed description of the performance and appearance of *Pittosporum tobira* 'Hines Hardy'. Descriptions are based on not less than 15 specimens for each specified characteristic. Color determinations are all based on The Royal Horticultural Society Colour Chart.

Overall size and growth chart:

*Size.*—The ultimate size of *Pittosporum tobira* 'Hines Hardy' is unknown as no specimen has reached full maturity.

*Habit.*—Mounding form, much branched and compact, as seen in the FIGURE.

Foliage:

*Apex.*—Obtuse.

*Arrangement.*—Alternate.

*Base.*—Narrowly cuneate.

*Margins.*—Entire and some are revolute.

*Shape.*—Obovate.

*Surface.*—Glabrous, coriaceous (mature foliage).

*Type.*—Broadleaf evergreen.

*Size.*—Length — (Petiole base to leaf apex) — 3.8 cm to 12.7 cm (1½" to 5") Width — 1.9 cm to 3.8 cm (¾" to 1½")

*Color.*—Upper leaf surface of mature leaves: R.H.S. Colour Chart, Fan 3, Green Group, No. 137 A. Lower leaf surface of mature leaves: R.H.S. Colour Chart, Fan 3, Yellow-Green Group, No. 146 C.

Flower: None observed.

Environmental tolerance: Hardiness. USDA Zone 8=10 to 20 degrees F. (Possibly USDA Zone 7=0 to 10 degrees F.)

The most significant desirable characteristic of *Pittosporum tobira* 'Hines Hardy' is its ability to withstand cold temperatures without damage. During January and February of 1982 the minimum temperature dropped to 10 degrees F. During this time period the temperature remained below freezing (32 degrees F.) for twenty-four consecutive hours at Hines Nursery site in Houston, Tex. During this freeze event, all the *Pittosporum tobira* were severely damaged or destroyed except one — *Pittosporum tobira* 'Hines Hardy'. The plant stood out as superior and appeared to be more compact.

In December of 1983 temperatures remained below 20 degrees F. for 17 consecutive hours. During late December 1983 and early January 1984 the minimum temperature dropped to a low of 13 degrees F. Temperatures remained below freezing for 123 consecutive hours (5.1 days). During this time period the original stock plant was a ten gallon container outdoors and did not exhibit any harmful effects either to the foliage or the root system.

During these two freeze events many other broadleaf evergreens growing at the same site were harshly injured or destroyed. These plants included *Pittosporum tobira* (USDA Zone 8), *Ilix cornuta* 'Burfordii' (USDA Zone 7) and *Photina×fraseri* (USDA Zone 7).

*Pittosporum tobira* 'Hines Hardy' has proven to be hardy to 10 degrees F. without any damage while other plants of the same species have not been able to demonstrate this ability.

I claim:

1. A new and distinct plant cultivar of *Pittosporum tobira* characterized by compact appearance and lustrous dark green foliage and having winter hardiness at least adequate for USDA Zone 8 (10°-20° F.).

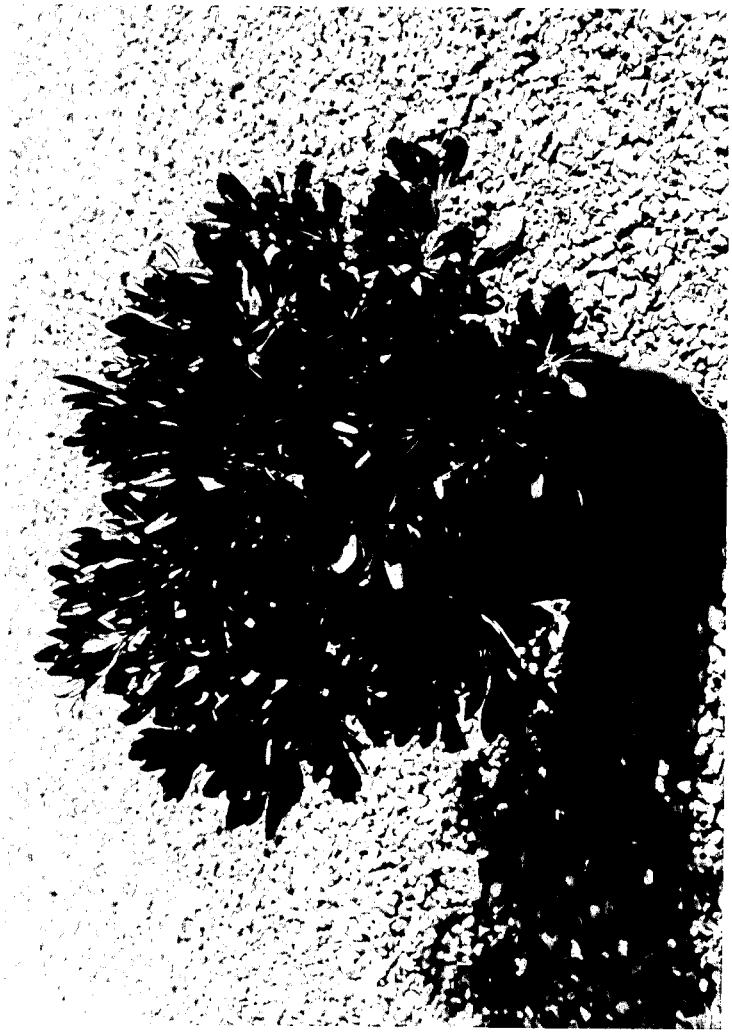

* * * * *